US00PP31593P3

(12) United States Plant Patent
Post

(10) Patent No.: US PP31,593 P3
(45) Date of Patent: Mar. 24, 2020

(54) ***CHRYSANTHEMUM* PLANT NAMED 'DLFARIS1'**

(50) Latin Name: ***Chrysanthemum* x *morifolium***
Varietal Denomination: DLFARIS1

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 16/501,361

(22) Filed: Mar. 29, 2019

(65) Prior Publication Data

US 2019/0307045 P1 Oct. 3, 2019

Related U.S. Application Data

(60) Provisional application No. 62/761,600, filed on Mar. 30, 2018.

(51) Int. Cl.
*A01H 5/02* (2018.01)
*A01H 6/14* (2018.01)

(52) U.S. Cl.
USPC ..... Plt./294
CPC ..... *A01H 6/1424* (2018.05)

(58) Field of Classification Search
USPC ..... Plt./294
CPC ..... A01H 5/02; A01H 6/14
See application file for complete search history.

*Primary Examiner* — Annette H Para
(74) *Attorney, Agent, or Firm* — C. A. Whealy

(57) ABSTRACT

A new and distinct cultivar of *Chrysanthemum* plant named 'DLFARIS1', characterized by its upright plant habit; vigorous growth habit; dark green-colored leaves; uniform and freely flowering habit; strong upright flowering stems with numerous inflorescences; single-type inflorescences with white-colored ray florets and bright yellow green-colored disc florets; and relative tolerance to high and low production temperatures.

2 Drawing Sheets

Botanical designation: *Chrysanthemum* x *morifolium*.
Cultivar denomination: 'DLFARIS1'.

BACKGROUND OF THE INVENTION

The present invention relates to a new and distinct cultivar of *Chrysanthemum* plant, botanically known as *Chrysanthemum* x *morifolium*, commercially grown as a cut flower and hereinafter referred to by the name 'DLFARIS1'.

The new *Chrysanthemum* plant is a product of a planned breeding program conducted by the Inventor in Maasdijk, The Netherlands. The objective of the breeding program is to create new freely-flowering cut *Chrysanthemum* plants with attractive inflorescences, strong flowering stems and excellent postproduction longevity.

The new *Chrysanthemum* plant originated from a cross-pollination made by the Inventor in Maasdijk, The Netherlands on Aug. 20, 2014, of a proprietary selection of *Chrysanthemum* x *morifolium* identified as code designation DB 10267, not patented, as the female, or seed, parent with a proprietary selection of *Chrysanthemum* x *morifolium* identified as code designation DB 11285, not patented, as the male, or pollen, parent. The new *Chrysanthemum* plant was discovered and selected by the Inventor as a single flowering plant from within the progeny of the stated cross-pollination in a controlled greenhouse environment in Maasdijk, The Netherlands on Apr. 15, 2015.

Asexual reproduction of the new *Chrysanthemum* plant by terminal vegetative cuttings in a controlled greenhouse environment in Maasdijk, The Netherlands since Apr. 15, 2015 has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFARIS1'. These characteristics in combination distinguish 'DLFARIS1' as a new and distinct *Chrysanthemum* plant:

1. Upright plant habit; vigorous growth habit.
2. Dark green-colored leaves.
3. Uniform and freely flowering habit.
4. Strong upright flowering stems with numerous inflorescences.
5. Single-type inflorescences with white-colored ray florets and bright yellow green-colored disc florets.
6. Relatively tolerant to high and low production temperatures.

Plants of the new *Chrysanthemum* differ from plants of the female parent selection in the following characteristics:

1. Leaf apices of plants of the new *Chrysanthemum* are more pointed than and not as round as leaf apices of plants of the female parent selection.
2. Ray florets of plants of the new *Chrysanthemum* are shorter and broader than ray florets of plants of the female parent selection.

Plants of the new *Chrysanthemum* differ from plants of the male parent selection in the following characteristics:

1. Ray florets of plants of the new *Chrysanthemum* are straight whereas ray florets of plants of the male parent selection are reflexed.
2. Plants of the new *Chrysanthemum* are more susceptible to White Rust (*Puccinia horiana*) than plants of the male parent selection.

Plants of the new *Chrysanthemum* can be compared to plants of *Chrysanthemum* x *morifolium* 'Bacardi', not patented. In side-by-side comparisons plants of the new *Chrysanthemum* differ from plants of 'Bacardi' in the following characteristics:

1. Ray florets of plants of the new *Chrysanthemum* are white in color whereas ray florets of plants of 'Bacardi' are creamy white in color when developing.
2. Disc florets of plants of the new *Chrysanthemum* are bright yellow green in color whereas disc florets of plants of 'Bacardi' are more yellow in color.

Plants of the new *Chrysanthemum* can also be compared to plants of *Chrysanthemum* x *morifolium* 'DLFESCE1 ', not patented. In side-by-side comparisons plants of the new *Chrysanthemum* differ from plants of 'DLFESCE1' in the following characteristics:

1. Leaves of plants of the new *Chrysanthemum* are longer than leaves of plants of 'DLFESCE1'.
2. Leaves of plants of the new *Chrysanthemum* have deeper sinuses than leaves of plants of 'DLFESCE1'.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'DLFARIS1' grown as a spray-type.

The photograph on the second sheet comprises close-up views of the lower (top of the photographic sheet) and upper surfaces (bottom of the photographic sheet) of typical inflorescences and leaves of 'DLFARIS1'.

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 20° C. to 25° C. and light levels averaged 8 klux. Plants were grown as single-stem plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* x *morifolium* 'DLFARIS1'.

Parentage:

*Female, or seed, parent.*—Proprietary selection of *Chrysanthemum* x *morifolium* identified as code designation DB 10267, not patented.

*Male, or pollen, parent.*—Proprietary selection of *Chrysanthemum* x *morifolium* identified as code designation DB 11285, not patented.

Propagation:

*Type.*—Terminal vegetative cuttings.

*Time to initiate roots, summer.*—About six days at temperatures about 24° C.

*Time to initiate roots, winter.*—About eight days at temperatures about 22° C.

*Time to produce a rooted young plant, summer.*—About twelve days at temperatures about 24° C.

*Time to produce a rooted young plant, winter.*—About two weeks at temperatures about 22° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous single daisy-type cut flower that is typically grown as a single stem spray-type; upright plant habit; vigorous growth habit and rapid growth rate.

*Plant height, soil level to top of foliar plane.*—About 78.4 cm.

*Plant height, soil level to top of inflorescence plane.*—About 81.8 cm.

*Plant (spray) diameter.*—About 19.8 cm.

*Flowering stem length.*—About 73 cm.

*Flowering stem diameter.*—About 7 mm.

*Flowering stem internode length.*—About 2.3 cm.

*Flowering stem strength.*—Strong.

*Flowering stem aspect.*—Erect.

*Flowering stem texture and luster.*—Slightly to moderately pubescent; slightly glossy.

*Flowering stem color, developing.*—Close to 144A, at the internodes, close to 146B.

*Flowering stem color, developed.*—Close to 146A and 146B.

*Leaf description.*—Arrangement: Alternate; simple. Length: About 12 cm. Width: About 8.7 cm. Shape: Broadly ovate. Apex: Short apiculate. Base: Attenuate. Margin: Palmately lobed, coarsely crenate; sinuses convergent and medium to deep in depth. Texture and luster, upper surface: Sparsely pubescent, not rugose; moderately velvety; very slightly glossy. Texture and luster, upper surface: Moderately pubescent, prominent venation; slightly velvety; matte. Venation pattern: Pinnate, reticulate. Color: Developing leaves, upper surface: Close to 143A. Developing leaves, lower surface: Close to between 146B and 146C. Fully developed leaves, upper surface: Close to NN137A; venation, close to 146B. Fully developed leaves, lower surface: Close to 147B; venation, close to 147C. Petioles: Length: About 1.8 cm. Diameter: About 3 mm by 4 mm. Strength: Moderately strong. Texture and luster, upper surface: Densely pubescent; moderately glossy. Texture and luster, lower surface: Densely pubescent; slightly glossy. Color, upper surface: Close to 148B; edges, close to NN137B. Color, lower surface: Close to 148C; edges, close to 147B. Stipules: Quantity and appearance: Two leafy stipules, opposite, at the petiole attachment to the stem. Length: About 1.5 cm. Width: About 1.3 cm.

Shape: Flabellate. Texture and luster, upper surface: Sparsely pubescent; very slightly glossy. Texture and luster, upper surface: Moderately pubescent; matte. Color, upper surface: Close to NN137A. Color, lower surface: Close to 147B.

Inflorescence description:

*Appearance.*—Single-type (daisy) inflorescence form with obovate-shaped ray florets and tubular disc florets; inflorescences borne perpendicular to peduncles and face mostly upright to slightly outwardly; ray and disc florets develop acropetally on a capitulum.

*Fragrance.*—Faintly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 50 days later when grown as a spray-type.

*Postproduction longevity.*—Good postproduction longevity; in an interior environment, inflorescences and foliage will maintain good color and substance for about two weeks; inflorescences persistent.

*Quantity of inflorescences.*—Freely flowering habit; when grown as a spray-type, about 16 inflorescences develop per flowering stem.

*Inflorescence size.*—Diameter: About 6.8 cm. Depth (height): About 2.1 cm. Disc diameter: About 1.6 cm.

*Receptacles.*—Height: About 4 mm. Diameter: About 6 mm. Shape: Flattened globular. Color: Close to 147D.

*Inflorescence buds.*—Height: About 1.4 cm. Diameter: About 1.4 cm. Shape: Roughly globular. Texture and luster: Distally, smooth and glabrous; proximally, slightly pubescent; very slightly glossy. Color: Distally, close to 155C (immature ray florets); proximally, close to 143A and 143B.

*Ray florets.*—Quantity and arrangement: About 16 arranged in about two whorls. Length: About 3.5 cm. Width: About 1.6 cm. Shape: Obovate; very slightly convex, moderately carinate. Apex: Broadly acute. Base: Attenuate. Margin: Entire; not undulate. Aspect: Initially upright to about 65° from vertical. Texture and luster, upper surface: Smooth, glabrous; moderately velvety; matte. Texture and luster, lower surface: Smooth, glabrous; moderately velvety; slightly glossy. Color: When opening, upper and lower surfaces: Close to NN155D. Fully opened, upper and lower surfaces: Close to NN155D; venation, close to NN155D; color does not change with development.

*Disc florets.*—Quantity and arrangement: About 220 spirally arranged in about eight whorls at the center of the receptacle. Length: About 6.5 mm. Diameter: About 1.8 mm. Shape: Lower 75% fused into a tube; upper 25% free. Apex: Acute. Margin: Entire. Texture and luster, inner and outer surfaces: Smooth, glabrous; glossy. Color, when opening, inner and outer surfaces: Apex: Close to 144A. Mid-section: Close to 154C. Base: Close to 145C. Color, fully opened, inner and outer surfaces: Apex: Close to 145A. Mid-section: Close to 154B to 154C. Base: Close to 145C to 145D.

*Involucral bracts.*—Quantity and arrangement: About 22 arranged in two whorls. Length: About 1 cm. Width: About 4 mm. Shape: Ovate. Apex: Obtuse. Base: Cuneate. Margin: Entire. Texture and luster, upper surface: Smooth, glabrous; glossy. Texture and luster, lower surface: Sparsely to moderately pubescent; very slightly glossy. Color, upper surface: Close to 143A; margins, translucent, and close to 157D; apices, close to N199A. Color, lower surface: Close to 137A to 137B; margins, translucent, close to 157D; apices, close to N199A.

*Peduncles.*—Length, terminal peduncle: About 4.2 cm. Diameter, terminal peduncle: About 3 mm. Length, third peduncle: About 6.1 cm. Diameter, terminal peduncle: About 3 mm. Strength: Strong. Aspect, terminal peduncle: Mostly upright. Aspect, third peduncle: About 45° from the flowering stem axis. Texture and luster: Moderately pubescent; matte. Color: Close to 143A.

*Reproductive organs.*—Androecium: Present on disc florets only. Quantity: About five per floret. Filament length: About 2 mm. Filament color: Close to 150D. Anther size: About 0.5 mm by 2 mm. Anther shape: Narrowly oblong. Anther color: Close to 12B. Pollen amount: Scarce. Pollen color: Close to 17B. Gynoecium: Present on both ray and disc florets. Quantity: One per floret. Pistil length: About 5 mm. Style length: About 4.5 mm. Style color: Close to N144B. Stigma diameter: About 1.5 mm. Stigma shape: Cleft, decurrent. Stigma color: Close to 6B. Ovary color: Close to 145B.

*Seeds and fruits.*—To date, seed and fruit production have not been observed on plants of the new *Chrysanthemum.*

Pathogen & pest resistance: Plants of the new *Chrysanthemum* have been observed to be resistant to *Fusarium* Wilt (*Fusarium oxysporum f.* sp. *chrysanthemi*) and *Verticillium* Wilt (*Puccinia horiana*). To date, resistance to pests and other pathogens common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFARIS1' as illustrated and described.

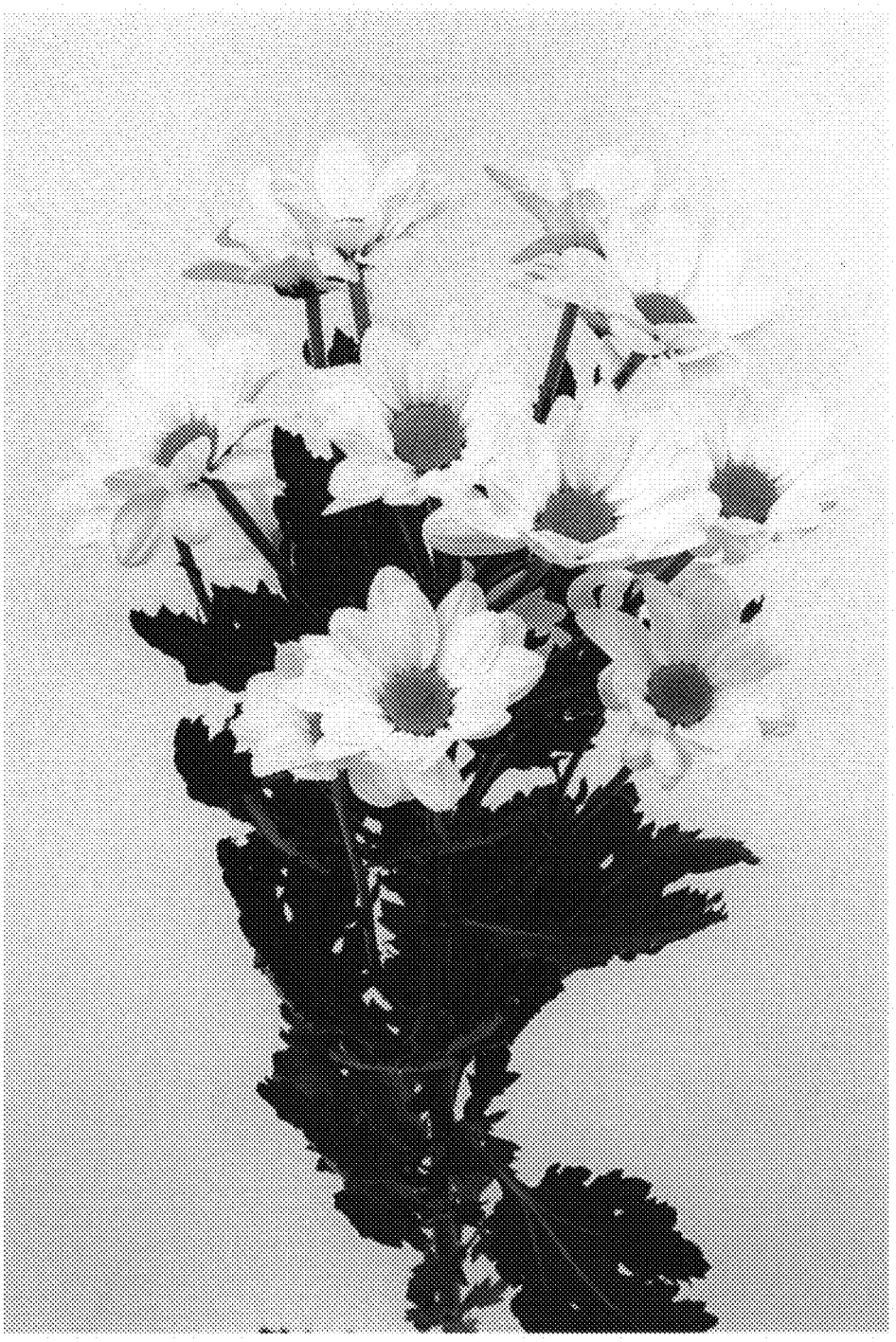

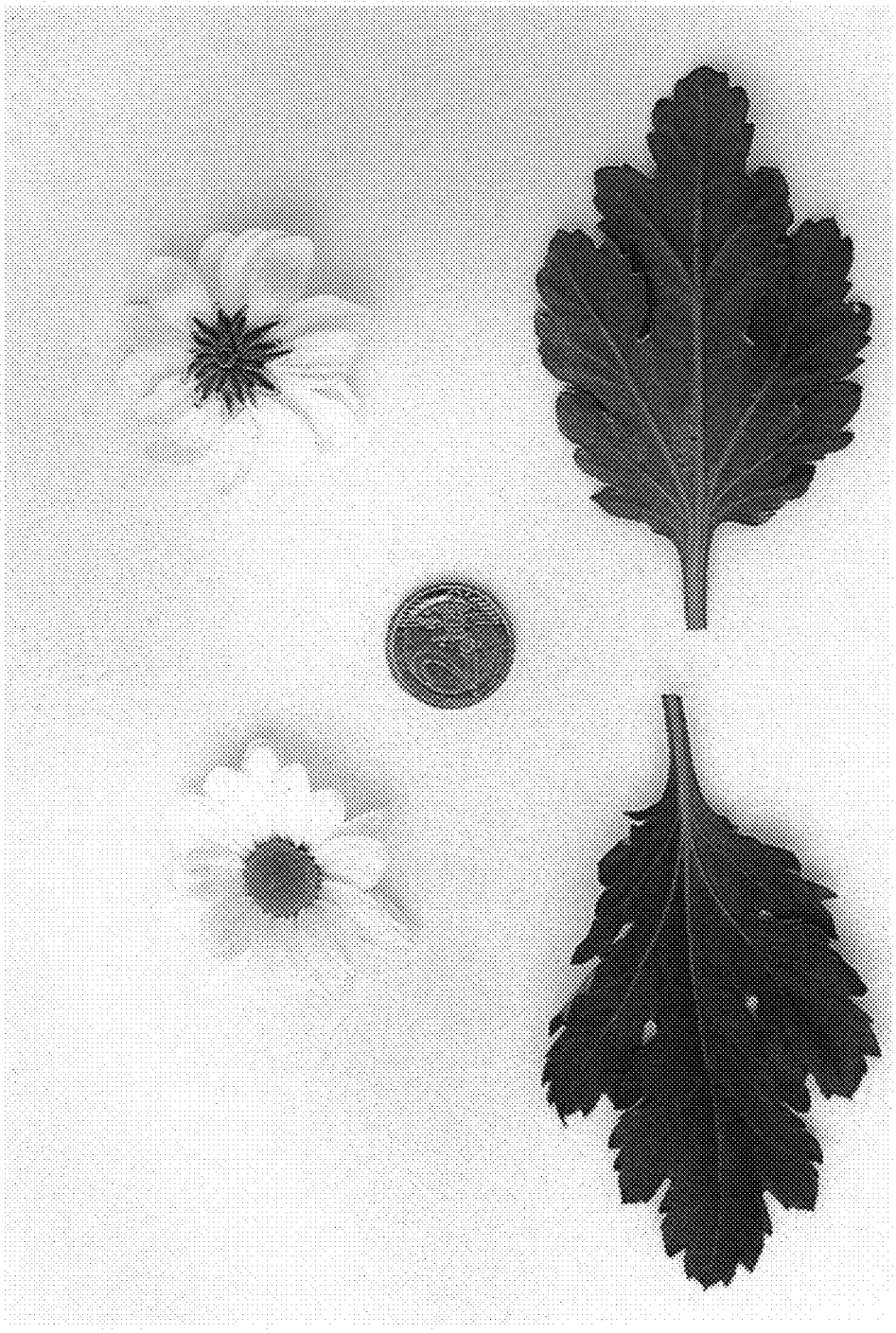

* * * * *